United States Patent [19]

Koyama et al.

[11] Patent Number: 5,391,821
[45] Date of Patent: Feb. 21, 1995

[54] PROCESS FOR PRODUCING CARBOXYLIC ACIDS

[75] Inventors: Hiroshi Koyama; Hidetaka Kojima, both of Himeji, Japan

[73] Assignee: Daicel Chemical Industries, Ltd., Osaka, Japan

[21] Appl. No.: 231,592

[22] Filed: Apr. 20, 1994

Related U.S. Application Data

[60] Continuation of Ser. No. 94,396, Jul. 19, 1993, abandoned, which is a continuation of Ser. No. 13,686, Feb. 4, 1993, abandoned, which is a division of Ser. No. 875,532, Apr. 27, 1992, Pat. No. 5,214,203, which is a continuation of Ser. No. 861,663, May 5, 1986, abandoned, which is a continuation of Ser. No. 643,227, Aug. 21, 1984, abandoned.

[30] Foreign Application Priority Data

Sep. 2, 1983 [JP] Japan ................. 58-161669

[51] Int. Cl.⁶ ................. C07C 45/50; C07C 51/12
[52] U.S. Cl. ................. 562/519
[58] Field of Search ................. 562/519

[56] References Cited

U.S. PATENT DOCUMENTS

| | | | |
|---|---|---|---|
| 3,487,112 | 12/1969 | Paulik et al. | 562/519 X |
| 3,769,326 | 10/1973 | Paulik et al. | 560/232 |
| 3,769,329 | 10/1973 | Paulik et al. | 560/232 |
| 3,813,428 | 5/1974 | Paulik et al. | 560/232 |
| 4,328,125 | 5/1982 | Drago et al. | 562/519 |
| 4,690,912 | 9/1987 | Paulik et al. | 502/161 |
| 4,733,006 | 3/1988 | Singleton | 562/519 X |
| 5,026,908 | 6/1991 | Smith et al. | 562/519 |

*Primary Examiner*—Arthur C. Prescott
*Attorney, Agent, or Firm*—Flynn, Thiel, Boutell & Tanis

[57] ABSTRACT

Carboxylic acids are produced in the liquid phase carbonylation reaction from an alcohol or its derivative and carbon monoxide in the presence of a catalyst system containing a rhodium component and an alkyl halide and water, adding an iodide salt to the rhodium/alkyl halide catalyst system so as to maintain the iodine ion concentration in the carbonylation reaction solution at 0.3 mol/l or higher.

99 Claims, 1 Drawing Sheet

PROCESS FOR PRODUCING CARBOXYLIC ACIDS

This application is a continuation of U.S. Ser. No. 08/094,396, filed Jul. 19, 1993, now abandoned, which is a continuation of U.S. Ser. No. 08/013,686, filed Feb. 4, 1993, now abandoned, which is a division of application Ser. No. 07/875,532, filed Apr. 27, 1992, now U.S. Pat. No. 5,214,203, which is a continuation of Ser. No. 06/861,663, filed May 5, 1986, now abandoned, which is a continuation of Ser. No. 06/643,227, filed Aug. 21, 1984, now abandoned.

The present invention relates to a process for producing carboxylic acids such as acetic acid. The carboxylic acids are useful chemicals having a high industrial value. Particularly, acetic acid has been produced on a commercial basis by, for example, carbonylation of methanol.

A process for producing carboxylic acids and esters thereof by reacting an alcohol or its derivative with carbon monoxide in the presence of a rhodium compound and a halogen compound has been known from, for example, the specification of Japanese Patent Publication No. 3334/1972. Usually, the alcohol is charged as such in the reaction system as the starting material. A reaction scheme for the reaction is shown as if the alcohol is reacted with carbon monoxide to form a carboxylic acid or its ester. However, from the viewpoint of the reaction mechanism, it has been believed that the carbonylation reaction proceeds via an alkyl halide [see Ind. Eng. Chem. Prod. Res. Dev., 15 (1), 46 (1976)]. It has also been known that the carboxylic acids or esters thereof can be obtained not only from the alcohols but also from alcohol derivatives capable of forming alkyl halides in the reaction system, such as esters or ethers. In the process of the present invention for producing carboxylic acids and esters thereof, the starting materials to be charged in the reaction system are not limited to the alcohols but they include also alcohol derivatives such as alkyl esters, alkyl ethers and alkyl halides. Non-limitative examples of the reactants include alcohols such as methanol, ethanol, propanol, butanol, 1,3-propanediol and 1,4-butanediol; esters such as methyl acetate, methyl propionate and ethyl propionate; halides such as methyl iodide, methyl bromide, ethyl iodide and ethyl bromide; ethers such as dimethyl ether, diethyl ether and methyl ethyl ether; and other alcohols and derivatives thereof as disclosed in the specification of Japanese Patent Publication No. 3334/1972.

A catalytic amount of a rhodium compound is used in the carbonylation reaction. It is believed that the rhodium compound is present in the reaction system in the form of a halogenorhodium carbonyl complex, i.e. rhodium coordinated with a halogen and carbon monoxide, having a catalytic effect in the carbonylation reaction [see, for example, Adv. Organometall. Chem., 17, 255 (1979)]. It has also been found that rhodium compounds other than the halogenorhodium carbonyl complexes are also converted into the halogenorhodium carbonyl complexes under the reaction conditions [see, for example, Adv. Organometall. Chem., 17, 255 (1979)]. The rhodium components herein are not limited to halogenorhodium carbonyls but other rhodium compounds are included therein. As non-limitative examples of the rhodium components to be used in the present invention, there may be mentioned $RhX_3$ (wherein X is Cl, Br or I), $RhX_3 \cdot 3H_2O$ (wherein X is Cl or Br), $Rh_2(CO)_{16}$, $Rh(CO)X[(C_6H_5)_3M]_2$ (wherein X is Cl, Br or I and M is P, As or Sb), $Rh(CO)_2X[(C_6H_5)_3M]$ (wherein X is Cl, Br or I and M is P, As or Sb), $HRh(Co)[(C_6H_5)_3P]_3$, $[Rh(C_2H_4)_2Cl]_2$ and $K_4Rh_2X_2(SnX_3)_4$ (wherein X is Cl, Br or I) and those disclosed in the specification of Japanese Patent Publication No. 3334/1972.

It has been known that, in the conventional carbonylation reactions, a water gas shift reaction (hereinafter referred to simply as shift reaction) occurs as a side reaction in addition to the main carbonylation reaction [see, for example, Adv. organometall. chem., 17, 255, (1979)]. In the shift reaction, carbon monoxide is reacted with water to form carbon dioxide and hydrogen as shown in formula (1):

$$CO + H_2O \rightarrow CO_2 + H_2 \qquad (1)$$

It has also been known that the reactant alcohol is hydrogenated by the hydrogen formed in the shift reaction as shown in formula (2): [see, for example, J. Organometall. Chem., 236, C-23 (1982)]:

$$ROH + H_2 \rightarrow RH + H_2O \qquad (2)$$

wherein R represents an alkyl group.

Thus, the conventional processes for the carbonylation reaction have serious defects that the carbon monoxide is lost due to the shift reaction and that hydrogen thus formed invites a loss of another starting material, i.e. the alcohol.

Further, by-production of carbon dioxide and hydrogen gas, resulting from the shift reaction, increases the gas pressure in the carbonylation and thereafter it is required to purge a part of the gas and depress the increase of the gas pressure.

After intensive investigations made for the purpose of overcoming those defects of the conventional processes for the carbonylation reaction, the inventors have found that when an extremely large amount of an iodide salt is incorporated in the reaction solution in addition to the alkyl halide, the side reactions can be controlled remarkably and, surprisingly, the carbonylation reaction rate is improved. The present invention has been completed on the basis of this finding.

The present invention provides a process for producing carboxylic acids by a liquid phase carbonylation reaction of an alcohol or its derivative with carbon monoxide carried out in the presence of a catalyst system containing a rhodium component and an alkyl halide which is an alkyl iodide or bromide and water, characterized in that an iodide salt is added to the rhodium-/alkyl halide catalyst system so as to maintain the iodine ion concentration in the carbonylation reaction solution at 0.3 mol/l or higher.

According to the present invention, the above-mentioned defects of the conventional carbonylation processes can be largely overcome and the carbonylation rate can be increased to improve the productivity. It has been known that the carbonylation reaction rate is proportional primarily to the rhodium concentration in the reaction solution [see, for example, Ind. Eng. Chem., Prod. Res. Dev., 15 (1), 46 (1976)]. According to the present invention, the amount of the expensive rhodium component can be reduced.

The carbonylation reaction in the conventional processes, too, is effected in the presence of a halide such as an iodide. However, the major part of the halide is present in the form of an alkyl halide which is an actual reactant to be carbonylated. Namely, the major part of the halide comprises a nonionic compound such as methyl iodide. Ionic halogen compounds comprise mainly hydrogen halide formed in a very small amount by the hydrolysis of the alkyl halide in the reaction system in general.

In some prior-art disclosures related to the above reaction, it is described that the halogen compounds may be used in the form of various precursors such as metal halides. However, as will be shown in Examples 27 and 28 given below, when sodium iodide or potassium iodide is used alone as the halogen source, the carbonylation reaction does not proceed in a heating time equal to a standard one employed when methyl iodide is used (i.e. in 70 min after initiation of the heating). It is also described in J. Mol. Catal. 16, 299 (1982) that an iodine source (such as an alkali metal iodide) incapable of forming a quite large amount of methyl iodide in the reaction system does not function as an accelerator for the reaction.

Apart from the subject of the carbonylation reaction accelerators, the description will be made on the prior techniques of producing carboxylic acids by carbonylation. A process has been known wherein a stabilizer is used in an amount necessary for maintaining the rhodium component in its soluble form (see Japanese Patent Laid-Open No. 134,436/1982). Among various stabilizers listed in this specification are alkali metal compounds and, in fact, 0.2 mol/l of potassium iodide is added to a model liquid in the separation step in Example 19 given in said specification. This prior invention is effective in preventing a reduction in amounts of dissolved rhodium under an insufficient CO condition by the addition of an alkali metal salt. However, the specification is silent on the influence of potassium iodide on the carbonylation reaction effected under an elevated CO pressure.

Thus, it has not been disclosed in the prior art wherein potassium iodide was used that the carbonylation reaction could be accelerated by adding an iodide salt to a rhodium/alkyl iodide catalyst system.

According to the present invention, an iodide salt is added to a combination of rhodium and an alkyl halide which are indispensable components of the fundamental carbonylation reaction catalyst system to realize a particularly high iodine ion concentration in the reaction solution to thereby accelerate the main reaction of forming a carboxylic acid from an alcohol while side reactions such as shift reactions are inhibited.

The description has been made on the alcohols and derivatives thereof used as the starting material, rhodium compounds used as the catalyst and alkyl halides indispensable as the accelerator used in the present invention with reference to the prior techniques. In other words, alcohols or derivatives thereof, rhodium compounds and alkyl halides which have been used in the state of the art may be used also in the invention.

The carboxylic acid which is the product of the present invention is obtained frequently in the form of its ester formed by a reaction thereof with the starting alcohol. Even though water is not charged in the reaction system, water formed by the esterification reaction is contained in the system. The term "the presence of water" in the production of carboxylic acid involves also such a case. However, the carbonylation of an ester or ether in the absence of water to form an acid anhydride is clearly distinguished from the above-mentioned reaction.

The iodide salts to be used in the present invention include the following compounds (a) and (b):

(a) metal iodides of formulae (3) and (4):

$$M_1 I_n \qquad (3)$$

$$M_1 I_{n+2} \qquad (4)$$

wherein $M_1$ represents a metal having a valence of n, and (b) onium-type iodides containing Group Va elements of the Periodic Table represented by formulae (5) and (6):

$$\left( \begin{array}{c} R_1 \\ R_2-M_2-R_4 \\ R_3 \end{array} \right)^+ I^- \qquad (5)$$

$$\left( \begin{array}{c} R_1 \\ R_2 \ M_2-R_4 \\ R_3 \end{array} \right)^+ I_3^- \qquad (6)$$

wherein $M_2$ represents a Group Va element of the Periodic Table and $R_1$ to $R_4$ represent each a hydrogen atom or an alkyl or aryl group.

Non-limitative examples thereof include LiI, NaI, KI, RbI, CsI, BeI$_2$, MgI$_2$, CaI$_2$, KI$_3$, CsI$_3$, NH$_4$I$_3$, GaI$_3$, CrI$_3$, MnI$_2$, LiI·3H$_2$O, MgI$_2$·8H$_2$O, NH$_4$I, N(CH$_3$)$_4$I, N(C$_6$H$_5$)$_4$I, NH$_3$CH$_3$I, PH$_4$I, P(CH$_3$)$_4$I, P(C$_6$H$_5$)$_4$I, P(C$_6$H$_5$)$_3$CH$_3$I, AsH$_4$I, As (CH$_3$)$_4$I, As(C$_6$H$_5$)$_4$I and As (C$_6$H$_5$)$_3$CH$_3$I.

Hydrogen iodide itself contains ionic iodine and is present in the reaction liquid in the conventional techniques. However, it reacts with an alkanol derivative to form an alkyl iodide to form an equilibrium mixture and, therefore, even if hydrogen iodide alone is added in a very large amount, the iodine ion concentration in the reaction liquid cannot be increased correspondingly.

Aluminum iodide is unsuitable for use in this process, since it reacts with the carboxylic acid in the reaction solution to form aluminum carboxylic and hydrogen iodide and a high concentration of the iodine ion in the reaction mixture cannot be maintained.

Further, salts of transition metal ions of iron group (Fe, Co and Ni) are not preferred as well, since they accelerate the shift reaction.

The iodide salts may be charged in the reaction system in the form of precursors from which the iodide salts can be formed under the reaction conditions. Precursors containing iodine component of the iodide salt are hydrogen iodide and organic iodides such as alkyl iodides which can be convered into hydrogen iodide in the reaction system. Precursors containing cationic component of the iodide salt include the following compounds (c) to (g):

(c) metal hydroxides of formula (7):

$$M_3(OH)_n \qquad (7)$$

wherein $M_3$ represents a metal having a valency of n,

(d) carboxylic acid salts of formula (8):

$$M_4(O\overset{\overset{O}{\|}}{C}-R)_n \qquad (8)$$

wherein $M_4$ represents a metal having a valency of n and R represents a hydrogen atom or an alkyl or aryl group, (e) element metals and metal oxides, (f) trivalent compounds containing Group Va elements of the Periodic Table of formula (9):

wherein $M_5$ represents a Group Va element of the Periodic Table and $R_1$ to $R_3$ represent each a hydrogen atom or an alkyl or aryl group, and (g) other metal compounds As described above with reference to the selection of the metal iodides, a metal to be used as the cationic component should be selected from those excluding aluminum and iron group transition metals.

Precursors containing cationic component of the iodide salt include, as non-limitative examples, the following compounds:

LiOH, KOH, NaOH, Rb(OH), Cs(OH), Be(OH)$_2$, Mg(OH)$_2$, LiOAc, KOAc, Be(OAc)$_2$, Li, K, Na, Li$_2$O, K$_2$O, BeO, MgO, NH$_3$, NMe$_3$, N(C$_6$H$_5$)$_3$, PH$_3$, PMe$_3$, P(C$_6$H$_5$)$_3$, AsMe$_3$ and Sb(C$_6$H$_5$)$_3$.

According to the present invention, at least 0.3 mol/l of the iodine ion is present in the form of a stable iodide salt in the reaction system due to the presence of the above-mentioned cationic component.

According to the present invention, the carbonylation reaction of the reactant with carbon monoxide is effected in the presence of the catalyst system comprising the rhodium component, alkyl halide and iodide salt at a suitable temperature under a suitable pressure which will be referred to below to obtain the carboxylic acid or its ester.

The concentration of the rhodium component in the reaction liquid is $10^{-4}$ to $10^{-1}$ mol/l, preferably $10^{-3}$ to $5 \times 10^{-2}$ mol/l.

The concentration of the alkyl halide in the reaction liquid is in the range of $10^{-2}$ to 10 mol/l, preferably $10^{-1}$ to 2 mol/l.

The amount of the iodide salt to be added is selected at will so as to attain an iodine ion concentration in the reaction liquid of at least 0.3 mol/l and the maximum amount is that for forming a saturated solution. Preferably, the iodide salt is used within an amount range of from 0.5 mol/l to the solubility.

Water is an indispensable component of the reaction system to form a carboxylic acid from an alkyl halide formed by the carbonylation of the alkyl halide in the reaction system. A hydrogen halide formed in this step is reacted with the alcohol to form the alkyl halide again and regenerate the water.

It has been known that the presence of water accelerates the formation of carboxylic acid also in the conventional processes wherein no iodide salt is used (see line 13, column 10 and line 6, column 15 in the specification of Japanese Patent Publication No. 3334/1972). However, as the water concentration in the reaction liquid is increased, not only the carbonylation reaction but also side reactions suck as the formation of CO$_2$ and CH$_4$ are accelerated remarkably (see Table 2).

The above-mentioned facts relating to the necessity of water and influences thereof apply also to the present invention. The presence of water is effective also for keeping a desired concentration of a water-soluble iodide such as an alkali metal iodide in the reaction system. The amount of water necessitated for this purpose is generally at least 1 mol/l in methyl acetate, though it varies depending on the composition. The effect of increasing the carbonylation rate can be obtained even when the water concentration is less than, 1 mol/l (see Example 21). However, in this case, a solid is contained in the reaction mixture after cooling.

Figure 1:
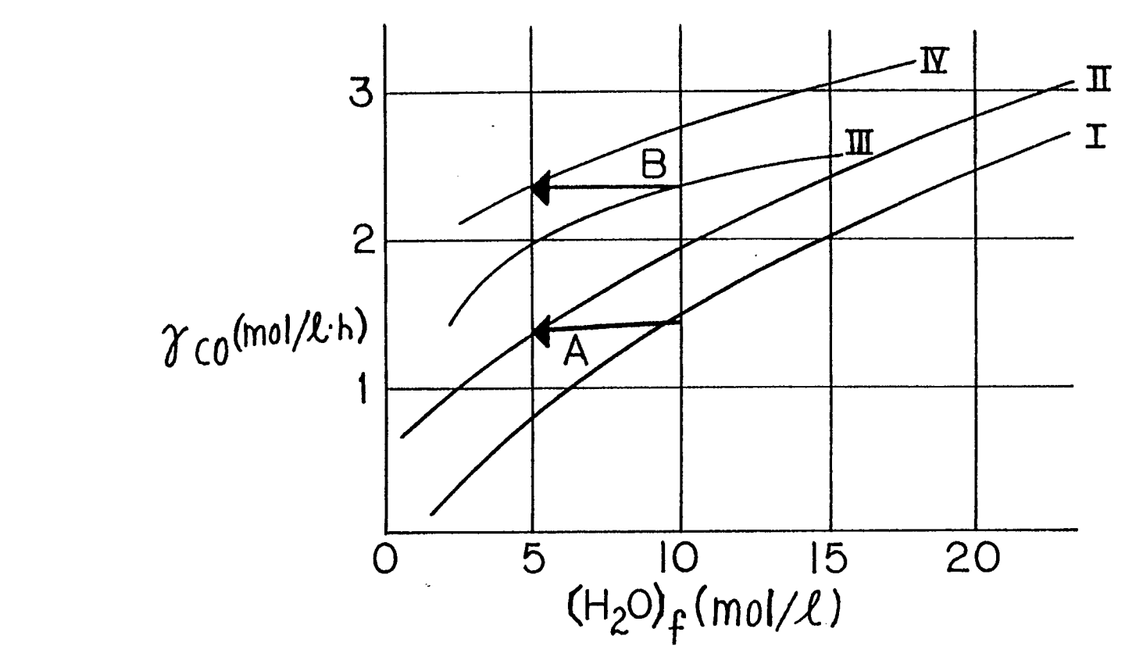
The drawing shows relationships between the water concentration ($[H_2O]f$) and the carbonylation reaction rate ($\gamma_{co}$mol/l·h) in the reaction of the present invention and comparative examples.

The effect of the added iodide salt in increasing the carbonylation reaction rate is recognized over a wide range of water concentration as shown in the drawing. As shown by an arrow A in the drawing, the addition of 0.6 mol/l of the iodide salt can reduce the water concentration to about 5 mol/l while the reaction rate is maintained almost equal to that realized when no iodide is used and a water concentration of 10 mol/l is used (see Tables 2 and 8 given below). The same inclination can be observed when the methanol concentration is altered (see an arrow B in the drawing and Table 10 given below).

In the conventional processes for producing carboxylic acids by carbonylation, the water concentration in the reaction liquid is generally up to about 20 mol/l, for example, 8 to 11 mol/l (15 to 20 wt. %; line 14, column 11 in the specification of Japanese Patent Publication No. 33428/1980). However, when the reaction is carried out in the presence of a smaller amount of water according to the present invention as described above, advantages such as an increase in the reaction selectivity (control of the formation of by-products such as CO$_2$ or CH$_4$ by the shift reaction) and reduction of energy consumption required for the separation of water in the purification process can be obtained.

When a water concentration equal to that employed in the conventional processes is employed in the present invention, the carbonylation reaction rate is higher than that realized in the conventional processes and the shift reaction can be controlled.

The water concentration employed in the present invention is generally at least 1 mol/l. The minimum water concentration with which no precipitate is formed varies depending on the composition of the reaction liquid and the type and amount of the iodide. When the methanol (in fact, present in the form of methyl acetate) concentration is high as in Example 21, the water concentration is relatively high. When the methanol concentration is low, a sufficiently homogeneous solution can be obtained with a water concentration of 1 mol/l. The upper limit of the water concentration is generally about 20 mol/l which is almost equal to that of the conventional processes. In view of both acceleration of the carbonylation reaction and control of the shift reaction, a particularly preferred water concentration is in the range of 3 to 10 mol/l.

The reaction temperature is in the range of 50° to 300° C., preferably 100° to 240° C.

The reaction pressure is such that the partial pressure of carbon monoxide is 0.05 to 1000 atm, preferably 0.3 to 300 atm and particularly 0.5 to 100 atm.

The reactant, i.e. an alcohol or its derivative, may be the same as that used in the prior techniques, e.g. that disclosed in the specification of Japanese Patent Publication No. 3334/1972. The alcohols include, for example, primary, secondary and tertiary aliphatic alcohols having 1 to 20 carbon atoms, such as methanol, ethanol, propanol, isopropyl alcohol, isobutanol and t-butyl alcohol; aromatic and alicyclic hydroxyl compounds having 6 to 20 carbon atoms; and polyhydric alcohols having 2 to 20 carbon atoms, such as 1,3-propylene glycol and 1,4-butanediol. Esters, ethers and halides of these alcohols may also be used as the starting alcohol derivatives in the present invention.

The alcohol concentration in the reaction solution may vary over a wide range according to the present invention. The alcohol in the reaction liquid may also be in the form of a carboxylic acid ester or alkyl halide formed by the reaction with the carboxylic acid or hydrogen halide and water in the reaction system. Therefore, the alcohol concentration in the reaction solution may refer to the total of the three compounds, i.e. the alcohol itself and two derivatives thereof. In the above-mentioned specification of Japanese Patent Laid-Open No. 134436/1982, the methanol concentration refers to the total concentration of methanol, methyl iodide and methyl acetate corresponding to "unstable methyl group". The total methanol concentration disclosed therein is 1.44 mol/l (suggesting that a major part thereof is methyl iodide, since the total iodide concentration is 1.40 mol/l).

Such an alcohol (including derivatives) concentration of around 1 mol/l is most commonly employed in the continuous production of the carboxylic acids. However, in the following examples, a higher alcohol concentration is employed so as to facilitate the determination of changes in the carbonylation and side reaction rates by effecting experimental batch reactions and analyzing the reaction liquid and gas. It is to be noted, however, that no essential difference lies between the results of the following examples and those of the continuous reaction effected with a lower alcohol concentration of around 1 mol/l. (it has been known that the carbonylation reaction is a zeroth-order reaction with respect to the alcohol concentration).

The following examples will further illustrate the present invention, which by no means limit the invention.

EXAMPLE 1 (Comparative Example)

Acetic acid was produced by carbonylating methanol in the presence of a fundamental catalyst comprising only a rhodium component and methyl iodide but free of any iodide salt. The experiment was effected as follows:

Compounds shown in the following Table 1 (107 ml in total) were charged in a 400-ml Hastelloy B autoclave provided with an agitator. Carbon monoxide was introduced therein to elevate the pressure to 40 kg/cm$^2$G.

TABLE 1

| Compound | Amount |
| --- | --- |
| $RhCl_3 \cdot 3H_2O$ | 0.24 mmol |
| $H_2O$ | 1.02 mol |
| $CH_3OH$ | 1.24 mol |
| $CH_3I$ | 0.080 mol |
| $CH_3CO_2H$ | 0.59 mol |

The mixture was heated under stirring. About 15 min after the initiation of the heating, the temperature of the reaction solution reached 185° C. Then, the temperature was maintained at 185° C. A gas absorption rate in a period of 45 to 75 min after the initiation of the heating was measured on the basis of the liquid temperature. The carbonylation reaction rate was determined from the gas absorption rate. 70 min after the initiation of the heating, the autoclave was cooled and the quantities of carbon dioxide and methane in the autoclave were determined according to gas chromatography. After completion of the reaction, the water concentration in the solution was 14.6 mol/l and the iodine ion concentration (hereinafter referred to as $[I^\ominus]_f$) was 0.033 mol/l. The rates of the reaction carried out in the absence of the iodide salt were as follows:

carbonylation reaction rate (hereinafter referred to as $\gamma_{co}$): 1.96 mol/l·h $CO_2$—formation reaction rate (hereinafter referred to as $\gamma_{CO_2}$): 18.9 mmol/l·h $CH_4$—formation reaction rate (hereinafter referred to as $\gamma_{CH_4}$): 9.39 mmol/l·h

EXAMPLE 2 (Referential example showing influences of water concentration)

The same procedure as in example 1 was repeated except that a part of the methanol was replaced with methyl acetate or the amount of water charged was altered to alter the water concentration in the reaction system. The same amounts of the rhodium compound and methyl iodide as in Example 1 were used but the amount of acetic acid charged was controlled to maintain the total amount of the solution at 107 ml. The manner of the reaction was also the same as in Example 1 except that the gas absorption rate was measured on the basis of gas temperature, and the autoclave was air-cooled to 100° C. 70 min after the initiation of the heating and then cooled with ice/water.

The results are shown in Table 2. It is understood that $\gamma_{co}$ was increased in proportion to the water concentration in the reaction system and that in a region of a high water concentration, the amounts of $CO_2$ and $CH_4$ formed by the shift reaction were increased remarkably. When no iodide salt was used, the iodine ion concentration which was increased as the water concentration was increased was generally up to 0.1 mol/l and even when the water concentration was extremely high, the concentration was up to 0.2 mol/l. A relationship between the water concentration and the carbonylation reaction rate obtained from the data in Table 2 is shown by curve I in FIG. 1.

TABLE 2

| Water con. (immediately after completion of reaction) mol/l | $\gamma CO$ mol/l·h | $\gamma CO_2$ mmol/l·h | $\gamma CH_4$ mmol/l·h | $[I^\ominus]_f$ mol/l |
| --- | --- | --- | --- | --- |
| 0.7 | 0 | 0.75 | 0 | 0.003 |
| 5.9 | 0.82 | 3.65 | 1.72 | 0.008 |
| 7.3 | 1.15 | 6.02 | 3.43 | 0.011 |
| 11.0 | 1.63 | 13.83 | 7.27 | 0.027 |
| 14.6 | 2.03 | 21.29 | 10.28 | 0.059 |
| 22.8 | 2.61 | 36.99 | 17.86 | 0.175 |

When the same procedure as in Example 1 was repeated except that the water concentration was varied, substantially similar results as in Example 1 were obtained as shown in Table 3. When the reaction mixture was cooled rapidly, the amount of the shift reaction products was reduced slightly but it was still larger than that of the first order proportion of water concentration.

The data of $[I^\ominus]_f$ in Table 2 are slightly higher than those shown in Table 3. It is probably because an HI-forming reaction occurred in the course of the slow cooling. Therefore, to determine the iodine ion concentration in the reaction liquid exactly, it is recommended to rapidly cool a small amount of the sample.

TABLE 3

| Water con. (immediately after completion of reaction) mol/l | $\gamma CO$ mol/l·h | $\gamma CO_2$ mmol/l·h | $\gamma CH_4$ mmol/l·h | $[I^\ominus]_f$ mol/l |
|---|---|---|---|---|
| 10.96 | 1.67 | 10.28 | 6.46 | 0.014 |
| 14.60 | 1.96 | 18.38 | 9.39 | 0.033 |
| 18.06 | 2.10 | 23.31 | 12.12 | 0.046 |
| 20.66 | 2.63 | 25.46 | 13.58 | 0.066 |

EXAMPLES 3 TO 5

The same procedure as in Example 1 was repeated except that lithium iodide, LiI·3H$_2$O, in an amount as shown in Table 4 was used. The results thus obtained was subjected to the linear correction on the basis of the data shown in Table 3 so as to realize the same water concentration as in Example 1, since the water content of the reaction system was increased due to the water containing in LiI·3H$_2$O. The results obtained by this operation are shown in Table 4.

TABLE 4

| Ex. | Amount of LiI added mol/l | $\gamma CO$ mol/l·h | $\gamma CO_2$ mmol/l·h | $\gamma CH_4$ mmol/l·h | $[I^\ominus]_f$ mol/l |
|---|---|---|---|---|---|
| 3 | 0.318 | 2.15 | 7.38 | 1.85 | 0.324 |
| 4 | 0.620 | 2.33 | 6.43 | 1.33 | 0.622 |
| 5 | 0.847 | 2.49 | 6.15 | 1.31 | 0.833 |

Unlike the case of using no lithium iodide (Example 1), the carbonylation rate was increased in proportion to the iodide salt concentration (increasing rate: 0.45 mol/l·h·mol-iodide salt/l; the value not corrected according to water concentration: 0.79 ). This fact indicates that the side reactions are controlled remarkably (to less than ½ of $\gamma_{co2}$ and 1/5 of $\gamma_{CH4}$) by the addition of even a small amount of lithium iodide.

EXAMPLES 6 TO 9

The same procedure as in Example 1 was repeated except that NaI was added to the liquid starting material. The results are shown in Table 5.

TABLE 5

| Ex. | Amount of NaI added mol/l | $\gamma CO$ mol/l·h | $\gamma CO_2$ mmol/l·h | $\gamma CH_4$ mmol/l·h | $[I^\ominus]_f$ mol/l |
|---|---|---|---|---|---|
| 6 | 0.310 | 2.10 | 7.19 | 1.83 | 0.308 |
| 7 | 0.656 | 2.27 | 7.45 | 1.66 | 0.796 |
| 8 | 1.251 | 2.50 | 6.13 | 1.07 | 1.492 |
| 9 | 2.444 | 3.06 | 5.96 | 1.96 | 2.292 |

The addition of sodium iodide accelerated the carbonylation reaction proportionally (the increasing rate: 0.42 mol/l·h·mol-iodide/l). As in the case of using LiI, the side reactions were controlled by using small amounts of sodium iodide.

When no methyl iodide was added, no carboxylic acid could be obtained even when adding NaI (see Example 27).

EXAMPLES 10 TO 13

The same procedure as in Example 1 was repeated except that potassium iodide was added to the liquid starting material. The results are shown in Table 6 (a symbol * means that $[I^\ominus]_f$ could not be determined).

TABLE 6

| Ex. | Amount of KI added Mol/l | $\gamma CO$ mol/l·h | $\gamma CO_2$ mmol/l·h | $\gamma CH_4$ mmol/l·h | $[I^\ominus]_f$ mol/l |
|---|---|---|---|---|---|
| 10 | 0.325 | 2.10 | 9.35 | 2.45 | 0.326 |
| 11 | 0.612 | 2.26 | 7.43 | 1.94 | 0.601 |
| 12 | 1.245 | 2.38 | 6.51 | 1.46 | * |
| 13 | 2.512 | 2.68 | 6.77 | 3.06 | * |

It is understood from this table that the addition of potassium iodide accelerates the carbonylation reaction proportionally (increasing rate: 0.27) and controls the side reactions by using only small amounts of potassium iodide.

EXAMPLES 14 TO 17

The same procedure as in Example 1 was repeated except that NH$_4$I was added to the liquid starting material. The results are shown in Table 7.

TABLE 7

| Ex. | Amount of NH$_4$I added mol/l | $\gamma CO$ mol/l·h | $\gamma CO_2$ mmol/l·h | $\gamma CH_4$ mmol/l·h | $[I^\ominus]_f$ mol/l |
|---|---|---|---|---|---|
| 14 | 0.329 | 2.13 | 9.53 | 2.61 | 0.335 |
| 15 | 0.645 | 2.35 | 8.06 | 2.09 | * |
| 16 | 1.243 | 2.53 | 8.23 | 1.97 | 1.199 |
| 17 | 2.492 | 3.21 | 12.47 | 3.75 | 2.300 |

The addition of ammonium iodide accelerated the carbonylation reaction (increasing rate: 0.50). The side reactions were controlled by using only small amounts of ammonium iodide (when the amount of ammonium iodide was excessive, the $\gamma_{CO2}$ and $\gamma_{CH4}$ were increased slightly).

EXAMPLE 18

The same procedure as in Example 1 was repeated except that 0.321 mol/l of methyltriphenylphosphonium iodide [CH$_3$(C$_6$H$_5$)$_3$PI] was used. $\gamma_{co}$ was 2.11 mol/l·h and the side reaction rates were: $\gamma_{CO2}$ of 8.54 mmol/l·h and $\gamma_{CH4}$ of 1.60 mmol/l·h.

EXAMPLE 19

The same procedure as in Example 1 was repeated except that 0.612 mol/l of MgI$_2$ was used. $\gamma_{co}$ was 2.17 mol/l·h, $\gamma_{co2}$ was 7.77 mol/l·h, $\gamma_{CH4}$ was 1.89 mmol/l·h and $[I^\ominus]_f$ was 0.613 mol/l.

EXAMPLE 20

The same procedure as in Example 1 was repeated except that 0.610 mol/l of zinc iodide was added to the liquid starting material. $\gamma_{co}$ was 2.10 mol/l·h and $[I^\ominus]_f$ was 0.660 mol/l.

EXAMPLES 21 TO 26

The same procedure as in Example 2 was repeated except that sodium iodide was added to the liquid starting material to obtain the results shown in Table 8. A relationship between the water concentration and the carbonylation reaction rate obtained from the data shown in Table 8 is shown by curve II in FIG. 1.

TABLE 8

| Ex. | Amount of NaI added mol/l | Water conc. (after completion of the reaction mol/l | $[I^\ominus]f$ mol/l | $\gamma CO$ mol/l.h | $\gamma_1$ % | $\gamma CO_2$ mmol/l.h | $\gamma_2$ % | $\gamma CH_4$ mmol/l.h | $\gamma_3$ % |
|---|---|---|---|---|---|---|---|---|---|
| 21 | 0.600 | 0.7 | 0.581 | 0.63 |  | 0.81 | 108 | 0 | — |
| 22 | 0.645 | 5.9 | 0.641 | 1.49 | 182 | 2.01 | 56 | 0 | 0 |
| 23 | 0.627 | 7.2 | 0.613 | 1.63 | 142 | 2.74 | 46 | 0.06 | 1.7 |
| 24 | 0.646 | 10.9 | 0.640 | 1.90 | 117 | 5.29 | 39 | 0.48 | 6.6 |
| 25 | 0.653 | 13.9 | 0.654 | 2.25 | 111 | 10.57 | 50 | 1.86 | 18.1 |
| 26 | 0.704 | 22.9 | 0.780 | 3.07 | 118 | 21.67 | 59 | 7.01 | 39 |

$\gamma_1$ is a percentage of $\gamma_{co}$ in this example to $\gamma_{co}$ (expressed as 100) obtained at the equal water concentration shown in Table 2. Though the reaction hardly occurred in the absence of the iodide salt when the water concentration was 0.7 mol/l, a quite high-percentage was obtained in this example. The effect of the addition of NaI was particularly excellent when the water concentration was low. $\gamma_2$ and $\gamma_3$ were values concerning $\gamma_{co2}$ and $\gamma_{CH4}$, respectively, obtained in the same manner as above in comparison with those shown in Table 2. Thus, the shift reaction-controlling effect was observed. This effect was particularly remarkable when the water concentration was low.

EXAMPLES 27 and 28 (Comparative Examples)

The same procedure as in Example 1 was repeated except that methyl iodide was replaced with the following iodide to obtain the results shown in Table 9.

TABLE 9

| Ex. | Iodide salt | Amount mmol | $\gamma CO$ mol/l.h | $\gamma CO_2$ mmol/l.h | $\gamma CH_4$ mmol/l.h |
|---|---|---|---|---|---|
| 27 | NaI | 69.8 | 0 | 6.46 | 0 |
| 28 | KI | 66.1 | 0 | 5.30 | 0 |

Unlike the results of Example 1, the carbonylation reaction did not proceed at all when sodium iodide or potassium iodide was used alone as the halogen source.

EXAMPLES 29 TO 31

The same procedure as in Examples 21 to 26 was repeated except that the total amount of methanol and methyl acetate charged was reduced to 0.31 mol and NaI in an amount shown in Table 10 was used. In this procedure, 0.24 mmol of $RhCl_3 \cdot 3H_2O$ and 0.080 mol of methyl iodide were used and the total amount of acetic acid and water was controlled to 107 ml. The heating time was controlled so that 0.6 to 0.8 mol/l of unreacted starting material remained (51 to 60 min.)

The results are shown in Table 10.

TABLE 10

| Ex. | Amount of NaI added mol/l | Water conc. (after completion of the reaction) mol/l | $[I^\ominus]f$ mol/l | $\gamma CO$ mol/l.h | $\gamma_1$ % |
|---|---|---|---|---|---|
| 29 | 1.24 | 4.0 | 1.25 | 2.25 | 128 |
| 30 | 1.24 | 8.5 | 1.28 | 2.60 | 115 |
| 31 | 1.38 | 15.7 | 1.43 | 3.07 | 132 |

(Note)
$\gamma_1$ is a percentage of the above obtained $\gamma_{co}$ based on the $\gamma_{co}$ obtained at the same water concentration but in the absence of NaI.

A relationship between the water concentration and the carbonylation reaction rate obtained from the data shown in Table 10 is shown by curve IV in FIG. 1.

Curve III shows the results obtained by carrying out the reaction with a low methanol concentration in the absence of NaI in the same manner as in Examples 29 to 31.

The embodiments of the invention in which an exclusive property or privilege is claimed are defined as follows:

1. A process for producing a carboxylic acid, which comprises:

charging into a reactor an alcohol or reactive derivative thereof and a catalyst system consisting essentially of (1) a rhodium carbonylation catalyst, (2) an alkyl iodide or alkyl bromide and (3) an iodide salt selected from the group consisting of sodium iodide, potassium iodide and lithium iodide, effecting liquid phase carbonylation of said alcohol or reactive derivative thereof by contacting same with carbon monoxide, the amount of said salt being sufficient to continuously maintain from 0.5 mol of iodide ion per liter of the carbonylation reaction solution up to the saturation concentration of said salt in the carbonylation reaction solution during the carbonylation reaction, said iodide salt being effective to reduce the formation of by-products and to increase the carbonylation reaction rate, said carbonylation reaction solution containing from about 1 mol to about 20 mols of water and from about $10^{-2}$ mol to about 10 mols of said alkyl iodide or alkyl bromide, per liter of the carbonylation reaction solution.

2. A process as claimed in claim 1, in which said alcohol is methanol.

3. A process as claimed in claim 1, in which said iodide salt is sodium iodide.

4. A process as claimed in claim 1, in which said iodide salt is potassium iodide.

5. A process as claimed in claim 1, in which said iodide salt is lithium iodide.

6. A process for producing a carboxylic acid, which comprises:

charging into a reactor an alcohol or reactive derivative thereof and a catalyst system consisting essentially of (1) a rhodium carbonylation catalyst, (2) an alkyl iodide or alkyl bromide and (3) an iodide salt selected from the group consisting of sodium iodide, potassium iodide and lithium iodide, effecting liquid phase carbonylation of said alcohol or reactive derivative thereof by contacting same with carbon monoxide, the amount of said salt being sufficient to continuously maintain from 0.5 mol of iodide ion per liter of the carbonylation reaction solution up to the saturation concentration of said salt in the carbonylation reaction solution during the carbonylation reaction, said iodide salt being effective to reduce the formation of by-products and to increase the carbonylation reaction rate, said carbonylation reaction solution containing from about 3 mol to about 20 mols of water and from about $10^{-2}$ mol to about 10 mols of said alkyl iodide or alkyl bromide, per liter of the carbonylation reaction solution.

7. A process as claimed in claim 6, in which said alcohol is methanol.

8. A process as claimed in claim 6, in which said iodide salt is sodium iodide.

9. A process as claimed in claim 6, in which said iodide salt is potassium iodide.

10. A process as claimed in claim 6, in which said iodide salt is lithium iodide.

11. A process for producing a carboxylic acid, which comprises:
    charging into a reactor an alcohol or reactive derivative thereof and a catalyst system consisting essentially of (1) a rhodium carbonylation catalyst, (2) an alkyl iodide or alkyl bromide and (3) an iodide salt selected from the group consisting of sodium iodide, potassium iodide and lithium iodide, effecting liquid phase carbonylation of said alcohol or reactive derivative thereof by contacting same with carbon monoxide, the amount of said salt being sufficient to continuously maintain from 0.5 mol of iodide ion per liter of the carbonylation reaction solution up to the saturation concentration of said salt in the carbonylation reaction solution during the carbonylation reaction, said iodide salt being effective to reduce the formation of by-products and to increase the carbonylation reaction rate, said carbonylation reaction solution containing from about 3 mol to about 10 mols of water and from about $10^{-2}$ mol to about 10 mols of said alkyl iodide or alkyl bromide, per liter of the carbonylation reaction solution.

12. A process as claimed in claim 11, in which said alcohol is methanol.

13. A process as claimed in claim 11, in which said iodide salt is sodium iodide.

14. A process as claimed in claim 11, in which said iodide salt is potassium iodide.

15. A process as claimed in claim 11, in which said iodide salt is lithium iodide.

16. A process for producing a carboxylic acid, which comprises:
    charging into a reactor an alcohol or reactive derivative thereof and a catalyst system consisting essentially of (1) a rhodium carbonylation catalyst, (2) an alkyl iodide or alkyl bromide and (3) an iodide salt selected from the group consisting of sodium iodide, potassium iodide and lithium iodide, effecting liquid phase carbonylation of said alcohol or reactive derivative thereof by contacting same with carbon monoxide, the amount of said salt being sufficient to continuously maintain from 0.3 mol of iodide ion per liter of the carbonylation reaction solution up to the saturation concentration of said salt in the carbonylation reaction solution during the carbonylation reaction, said iodide salt being effective to reduce the formation of by-products and to increase the carbonylation reaction rate, said carbonylation reaction solution containing from about 1 mol to about 20 mols of water and from about $10^{-2}$ mol to about 10 mols of said alkyl iodide or alkyl bromide, per liter of the carbonylation reaction solution.

17. A process as claimed in claim 16, in which said alcohol is methanol.

18. A process as claimed in claim 16, in which said iodide salt is sodium iodide.

19. A process as claimed in claim 16, in which said iodide salt is potassium iodide.

20. A process as claimed in claim 16, in which said iodide salt is lithium iodide.

21. A process for producing a carboxylic acid, which comprises:
    charging into a reactor an alcohol or reactive derivative thereof and a catalyst system consisting essentially of (1) a rhodium carbonylation catalyst, (2) an alkyl iodide or alkyl bromide and (3) an iodide salt selected from the group consisting of sodium iodide, potassium iodide and lithium iodide, effecting liquid phase carbonylation of said alcohol or reactive derivative thereof by contacting same with carbon monoxide, the amount of said salt being sufficient to continuously maintain from 0.3 mol of iodide ion per liter of the carbonylation reaction solution up to the saturation concentration of said salt in the carbonylation reaction solution during the carbonylation reaction, said iodide salt being effective to reduce the formation of by-products and to increase the carbonylation reaction rate, said carbonylation reaction solution containing from about 3 mol to about 20 mols of water and from about $10^{-2}$ mol to about 10 mols of said alkyl iodide or alkyl bromide, per liter of the carbonylation reaction solution.

22. A process as claimed in claim 21, in which said alcohol is methanol.

23. A process as claimed in claim 21, in which said iodide salt is sodium iodide.

24. A process as claimed in claim 21, in which said iodide salt is potassium iodide.

25. A process as claimed in claim 21, in which said iodide salt is lithium iodide.

26. A process for producing a carboxylic acid, which comprises:
    charging into a reactor an alcohol or reactive derivative thereof and a catalyst system consisting essentially of (1) a rhodium carbonylation catalyst, (2) an alkyl iodide or alkyl bromide and (3) an iodide salt selected from the group consisting of sodium iodide, potassium iodide and lithium iodide, effecting liquid phase carbonylation of said alcohol or reactive derivative thereof by contacting same with carbon monoxide, the amount of said salt being sufficient to continuously maintain from 0.3 mol of iodide ion per liter of the carbonylation reaction solution up to the saturation concentration of said salt in the carbonylation reaction solution during the carbonylation reaction, said iodide salt being effective to reduce the formation of by-products and to increase the carbonylation reaction rate, said carbonylation reaction solution containing from about 3 mol to about 10 mols of water and from about $10^{-2}$ mol to about 10 mols of said alkyl iodide or alkyl bromide, per liter of the carbonylation reaction solution.

27. A process as claimed in claim 26, in which said alcohol is methanol.

28. A process as claimed in claim 26, in which said iodide salt is sodium iodide.

29. A process as claimed in claim 26, in which said iodide salt is potassium iodide.

30. A process as claimed in claim 26, in which said iodide salt is lithium iodide.

31. A process for producing a carboxylic acid, which comprises:
charging into a reactor an alcohol or reactive derivative thereof and a catalyst system consisting essentially of (1) a rhodium carbonylation catalyst, (2) an alkyl iodide or alkyl bromide and (3) an iodide salt selected from the group consisting of sodium iodide, potassium iodide and lithium iodide, effecting liquid phase carbonylation of said alcohol or reactive derivative thereof by contacting same with carbon monoxide, from 0.5 mol of iodide ion per liter of the carbonylation reaction solution being present in the carbonylation reaction solution, said iodide salt being effective to reduce the formation of by-products and to increase the carbonylation reaction rate, said carbonylation reaction solution containing from about 1 mol to about 20 mols of water and from about $10^{-2}$ mol to about 10 mols of said alkyl iodide or alkyl bromide, per liter of the carbonylation reaction solution.

32. A process as claimed in claim 31, in which said alcohol is methanol.

33. A process as claimed in claim 31, in which said iodide salt is sodium iodide.

34. A process as claimed in claim 31, in which said iodide salt is potassium iodide.

35. A process as claimed in claim 31, in which said iodide salt is lithium iodide.

36. A process for producing a carboxylic acid, which comprises:
charging into a reactor an alcohol or reactive derivative thereof and a catalyst system consisting essentially of (1) a rhodium carbonylation catalyst, (2) an alkyl iodide or alkyl bromide and (3) an iodide salt selected from the group consisting of sodium iodide, potassium iodide and lithium iodide, effecting liquid phase carbonylation of said alcohol or reactive derivative thereof by contacting same with carbon monoxide, from 0.5 mol of iodide ion per liter of the carbonylation reaction solution being present in the carbonylation reaction solution, said iodide salt being effective to reduce the formation of by-products and to increase the carbonylation reaction rate, said carbonylation reaction solution containing from about 3 mol to about 20 mols of water and from about $10^{-2}$ mol to about 10 mols of said alkyl iodide or alkyl bromide, per liter of the carbonylation reaction solution.

37. A process as claimed in claim 36, in which said alcohol is methanol.

38. A process as claimed in claim 36, in which said iodide salt is sodium iodide.

39. A process as claimed in claim 36, in which said iodide salt is potassium iodide.

40. A process as claimed in claim 37, in which said iodide salt is lithium iodide.

41. A process for producing a carboxylic acid, which comprises:
charging into a reactor an alcohol or reactive derivative thereof and a catalyst system consisting essentially of (1) a rhodium carbonylation catalyst, (2) an alkyl iodide or alkyl bromide and (3) an iodide salt selected from the group consisting of sodium iodide, potassium iodide and lithium iodide, effecting liquid phase carbonylation of said alcohol or reactive derivative thereof by contacting same with carbon monoxide, from 0.5 mol of iodide ion per liter of the carbonylation reaction solution being present in the carbonylation reaction solution, said iodide salt being effective to reduce the formation of by-products and to increase the carbonylation reaction rate, said carbonylation reaction solution containing from about 3 mol to about 10 mols of water and from about $10^{-2}$ mol to about 10 mols of said alkyl iodide or alkyl bromide, per liter of the carbonylation reaction solution.

42. A process as claimed in claim 41, in which said alcohol is methanol.

43. A process as claimed in claim 41, in which said iodide salt is sodium iodide.

44. A process as claimed in claim 41, in which said iodide salt is potassium iodide.

45. A process as claimed in claim 41, in which said iodide salt is lithium iodide.

46. A process for producing a carboxylic acid, which comprises:
charging into a reactor an alcohol or reactive derivative thereof and a catalyst system consisting essentially of (1) a rhodium carbonylation catalyst, (2) an alkyl iodide or alkyl bromide and (3) an iodide salt selected from the group consisting of sodium iodide, potassium iodide and lithium iodide, effecting liquid phase carbonylation of said alcohol or reactive derivative thereof by contacting same with carbon monoxide, from 0.3 mol of iodide ion per liter of the carbonylation reaction solution being present in the carbonylation reaction solution, said iodide salt being effective to reduce the formation of by-products and to increase the carbonylation reaction rate, said carbonylation reaction solution containing from about 1 mol to about 20 mols of water and from about $10^{-2}$ mol to about 10 mols of said alkyl iodide or alkyl bromide, per liter of the carbonylation reaction solution.

47. A process as claimed in claim 46, in which said alcohol is methanol.

48. A process as claimed in claim 46, in which said iodide salt is sodium iodide.

49. A process as claimed in claim 46, in which said iodide salt is potassium iodide.

50. A process as claimed in claim 46, in which said iodide salt is lithium iodide.

51. A process for producing a carboxylic acid, which comprises:
charging into a reactor an alcohol or reactive derivative thereof and a catalyst system consisting essentially of (1) a rhodium carbonylation catalyst, (2) an alkyl iodide or alkyl bromide and (3) an iodide salt selected from the group consisting of sodium iodide, potassium iodide and lithium iodide, effecting liquid phase carbonylation of said alcohol or reactive derivative thereof by contacting same with carbon monoxide, from 0.3 mol of iodide ion per liter of the carbonylation reaction solution being present in the carbonylation reaction solution, said iodide salt being effective to reduce the formation of by-products and to increase the carbonylation reaction rate, said carbonylation reaction solution containing from about 3 mol to about 20 mols of water and from about $10^{-2}$ mol to about 10 mols of said alkyl iodide or alkyl bromide, per liter of the carbonylation reaction solution.

52. A process as claimed in claim 51, in which said alcohol is methanol.

53. A process as claimed in claim 51, in which said iodide salt is sodium iodide.

54. A process as claimed in claim 51, in which said iodide salt is potassium iodide.

55. A process as claimed in claim 51, in which said iodide salt is lithium iodide.

56. A process for producing a carboxylic acid, which comprises:
charging into a reactor an alcohol or reactive derivative thereof and a catalyst system consisting essentially of (1) a rhodium carbonylation catalyst, (2) an alkyl iodide or alkyl bromide and (3) an iodide salt selected from the group consisting of sodium iodide, potassium iodide and lithium iodide, effecting liquid phase carbonylation of said alcohol or reactive derivative thereof by contacting same with carbon monoxide, from 0.3 mol of iodide ion per liter of the carbonylation reaction solution being present in the carbonylation reaction solution, said iodide salt being effective to reduce the formation of by-products and to increase the carbonylation reaction rate, said carbonylation reaction solution containing from about 3 mol to about 10 mols of water and from about $10^{-2}$ mol to about 10 mols of said alkyl iodide or alkyl bromide, per liter of the carbonylation reaction solution.

57. A process as claimed in claim 56, in which said alcohol is methanol.

58. A process as claimed in claim 56, in which said iodide salt is sodium iodide.

59. A process as claimed in claim 56, in which said iodide salt is potassium iodide.

60. A process as claimed in claim 56, in which said iodide salt is lithium iodide.

61. A process for producing a carboxylic acid, which comprises:
charging into a reactor an alcohol or reactive derivative thereof and a catalyst system consisting essentially of (1) a rhodium carbonylation catalyst, (2) an alkyl iodide or alkyl bromide and (3) an iodide salt selected from the group consisting of sodium iodide, potassium iodide and lithium iodide, effecting liquid phase carbonylation of said alcohol or reactive derivative thereof by contacting same with carbon monoxide, from 0.5 mol of iodide ion per liter of the carbonylation reaction solution being present in the carbonylation reaction solution, said iodide salt being effective to reduce the formation of by-products and to increase the carbonylation reaction rate, said carbonylation reaction solution containing from about 0.7 mol to about 5.9 mols of water and from about $10^{-2}$ mol to about 10 mols of said alkyl iodide or alkyl bromide, per liter of the carbonylation reaction solution.

62. A process as claimed in claim 61, in which said alcohol is methanol.

63. A process as claimed in claim 61, in which said iodide salt is sodium iodide.

64. A process as claimed in claim 61, in which said iodide salt is potassium iodide.

65. A process as claimed in claim 61, in which said iodide salt is lithium iodide.

66. A process for producing a carboxylic acid, which comprises:
charging into a reactor an alcohol or reactive derivative thereof and a catalyst system consisting essentially of (1) a rhodium carbonylation catalyst, (2) an alkyl iodide or alkyl bromide and (3) an iodide salt selected from the group consisting of sodium iodide, potassium iodide and lithium iodide, effecting liquid phase carbonylation of said alcohol or reactive derivative thereof by contacting same with carbon monoxide, from 0.5 mol up to the saturation level of iodide ion per liter of the carbonylation reaction solution being present in the carbonylation reaction solution, said iodide salt being effective to reduce the formation of by-products and to increase the carbonylation reaction rate, said carbonylation reaction solution containing from about 1 mol to about 20 mols of water and from about $10^{-2}$ mol to about 10 mols of said alkyl iodide or alkyl bromide, per liter of the carbonylation reaction solution.

67. A process as claimed in claim 66, in which said alcohol is methanol.

68. A process as claimed in claim 66, in which said iodide salt is sodium iodide.

69. A process as claimed in claim 66, in which said iodide salt is potassium iodide.

70. A process as claimed in claim 66, in which said iodide salt is lithium iodide.

71. A process for producing a carboxylic acid, which comprises:
charging into a reactor an alcohol or reactive derivative thereof and a catalyst system consisting essentially of (1) a rhodium carbonylation catalyst, (2) an alkyl iodide or alkyl bromide and (3) an iodide salt selected from the group consisting of sodium iodide, potassium iodide and lithium iodide, effecting liquid phase carbonylation of said alcohol or reactive derivative thereof by contacting same with carbon monoxide, from 0.5 mol up to the saturation level of iodide ion per liter of the carbonylation reaction solution being present in the carbonylation reaction solution, said iodide salt being effective to reduce the formation of by-products and to increase the carbonylation reaction rate, said carbonylation reaction solution containing from about 3 mol to about 20 mols of water and from about $10^{-2}$ mol to about 10 mols of said alkyl iodide or alkyl bromide, per liter of the carbonylation reaction solution.

72. A process as claimed in claim 71, in which said alcohol is methanol.

73. A process as claimed in claim 71, in which said iodide salt is sodium iodide.

74. A process as claimed in claim 71, in which said iodide salt is potassium iodide.

75. A process as claimed in claim 71, in which said iodide salt is lithium iodide.

76. A process for producing a carboxylic acid, which comprises:
charging into a reactor an alcohol or reactive derivative thereof and a catalyst system consisting essentially of (1) a rhodium carbonylation catalyst, (2) an alkyl iodide or alkyl bromide and (3) an iodide salt selected from the group consisting of sodium iodide, potassium iodide and lithium iodide, effecting liquid phase carbonylation of said alcohol or reactive derivative thereof by contacting same with carbon monoxide, from 0.5 mol up to the saturation level of iodide ion per liter of the carbonylation reaction solution being present in the carbonylation reaction solution, said iodide salt being effective to reduce the formation of by-products and to increase the carbonylation reaction rate, said carbonylation reaction solution containing from about 3 mol to about 10 mols of water and from about $10^{-2}$ mol to about 10 mols of said alkyl iodide or alkyl bromide, per liter of the carbonylation reaction solution.

77. A process as claimed in claim 76, in which said alcohol is methanol.

78. A process as claimed in claim 76, in which said iodide salt is sodium iodide.

79. A process as claimed in claim 76, in which said iodide salt is potassium iodide.

80. A process as claimed in claim 76, in which said iodide salt is lithium iodide.

81. A process for producing a carboxylic acid, which comprises:

charging into a reactor an alcohol or reactive derivative thereof and a catalyst system consisting essentially of (1) a rhodium carbonylation catalyst, (2) an alkyl iodide or alkyl bromide and (3) an iodide salt selected from the group consisting of sodium iodide, potassium iodide and lithium iodide, effecting liquid phase carbonylation of said alcohol or reactive derivative thereof by contacting same with carbon monoxide, from 0.3 mol up to the saturation level of iodide ion per liter of the carbonylation reaction solution being present in the carbonylation reaction solution, said iodide salt being effective to reduce the formation of by-products and to increase the carbonylation reaction rate, said carbonylation reaction solution containing from about 1 mol to about 20 mols of water and from about $10^{-2}$ mol to about 10 mols of said alkyl iodide or alkyl bromide, per liter of the carbonylation reaction solution.

82. A process as claimed in claim 81, in which said alcohol is methanol.

83. A process as claimed in claim 81, in which said iodide salt is sodium iodide.

84. A process as claimed in claim 81, in which said iodide salt is potassium iodide.

85. A process as claimed in claim 81, in which said iodide salt is lithium iodide.

86. A process for producing a carboxylic acid, which comprises:

charging into a reactor an alcohol or reactive derivative thereof and a catalyst system consisting essentially of (1) a rhodium carbonylation catalyst, (2) an alkyl iodide or alkyl bromide and (3) an iodide salt selected from the group consisting of sodium iodide, potassium iodide and lithium iodide, effecting liquid phase carbonylation of said alcohol or reactive derivative thereof by contacting same with carbon monoxide, from 0.3 mol up to the saturation level of iodide ion per liter of the carbonylation reaction solution being present in the carbonylation reaction solution, said iodide salt being effective to reduce the formation of by-products and to increase the carbonylation reaction rate, said carbonylation reaction solution containing from about 3 mol to about 20 mols of water and from about $10^{-2}$ mol to about 10 mols of said alkyl iodide or alkyl bromide, per liter of the carbonylation reaction solution.

87. A process as claimed in claim 86, in which said alcohol is methanol.

88. A process as claimed in claim 86, in which said iodide salt is sodium iodide.

89. A process as claimed in claim 86, in which said iodide salt is potassium iodide.

90. A process as claimed in claim 86, in which said iodide salt is lithium iodide.

91. A process for producing a carboxylic acid, which comprises:

charging into a reactor an alcohol or reactive derivative thereof and a catalyst system consisting essentially of (1) a rhodium carbonylation catalyst, (2) an alkyl iodide or alkyl bromide and (3) an iodide salt selected from the group consisting of sodium iodide, potassium iodide and lithium iodide, effecting liquid phase carbonylation of said alcohol or reactive derivative thereof by contacting same with carbon monoxide, from 0.3 mol up to the saturation level of iodide ion per liter of the carbonylation reaction solution being present in the carbonylation reaction solution, said iodide salt being effective to reduce the formation of by-products and to increase the carbonylation reaction rate, said carbonylation reaction solution containing from about 3 mol to about 10 mols of water and from about $10^{-2}$ mol to about 10 mols of said alkyl iodide or alkyl bromide, per liter of the carbonylation reaction solution.

92. A process as claimed in claim 91, in which said alcohol is methanol.

93. A process as claimed in claim 91, in which said iodide salt is sodium iodide.

94. A process as claimed in claim 91, in which said iodide salt is potassium iodide.

95. A process as claimed in claim 91, in which said iodide salt is lithium iodide.

96. A process for producing a carboxylic acid, which comprises:

charging into a reactor an alcohol or reactive derivative thereof and a catalyst system consisting essentially of (1) a rhodium carbonylation catalyst, (2) an alkyl iodide or alkyl bromide and (3) an iodide salt selected from the group consisting of sodium iodide, potassium iodide and lithium iodide, effecting liquid phase carbonylation of said alcohol or reactive derivative thereof by contacting same with carbon monoxide, from 0.5 mol up to the saturation level of iodide ion per liter of the carbonylation reaction solution being present in the carbonylation reaction solution, said iodide salt being effective to reduce the formation of by-products and to increase the carbonylation reaction rate, said carbonylation reaction solution containing from about 0.7 mol to about 5.9 mols of water and from about $10^{-2}$ mol to about 10 mols of said alkyl iodide or alkyl bromide, per liter of the carbonylation reaction solution.

97. A process as claimed in claim 96, in which said alcohol is methanol.

98. A process as claimed in claim 96, in which said iodide salt is sodium iodide.

99. A process as claimed in claim 96, in which said iodide salt is potassium iodide.

* * * * *

UNITED STATES PATENT AND TRADEMARK OFFICE
CERTIFICATE OF CORRECTION

PATENT NO. : 5 391 821
DATED : February 21, 1995
INVENTOR(S) : Hiroshi KOYAMA, et al.

It is certified that error appears in the above-indentified patent and that said Letters Patent is hereby corrected as shown below:

Column 15, line 57; change "37" to ---36---.
Column 20, line 65; insert ---100. A process as claimed in Claim 96, in which said iodide salt is lithium iodide.---.

Signed and Sealed this

Twentieth Day of June, 1995

Attest:

BRUCE LEHMAN

Attesting Officer

Commissioner of Patents and Trademarks